United States Patent
Choi et al.

(10) Patent No.: US 10,251,540 B2
(45) Date of Patent: Apr. 9, 2019

(54) APPARATUS AND METHOD FOR FIXING AND SHORTENING BOWEL AT THE TIME OF ENDOSCOPY

(71) Applicants: Jae-hong Choi, Chungcheongbuk-do (KR); Eun-jong Cha, Seoul (KR)

(72) Inventors: Jae-hong Choi, Chungcheongbuk-do (KR); Eun-jong Cha, Seoul (KR)

(*) Notice: Subject to any disclaimer, the term of this patent is extended or adjusted under 35 U.S.C. 154(b) by 106 days.

(21) Appl. No.: 14/909,986

(22) PCT Filed: Nov. 4, 2014

(86) PCT No.: PCT/KR2014/010530
§ 371 (c)(1),
(2) Date: Feb. 4, 2016

(87) PCT Pub. No.: WO2015/065163
PCT Pub. Date: May 7, 2015

(65) Prior Publication Data
US 2016/0198935 A1 Jul. 14, 2016

(30) Foreign Application Priority Data
Nov. 4, 2013 (KR) .................... 10-2013-0132907

(51) Int. Cl.
*A61B 1/04* (2006.01)
*A61B 1/31* (2006.01)
(Continued)

(52) U.S. Cl.
CPC .......... *A61B 1/31* (2013.01); *A61B 1/00082* (2013.01); *A61B 1/00087* (2013.01);
(Continued)

(58) Field of Classification Search
CPC ... A61B 1/00082; A61B 1/00154; A61B 1/31; A61B 1/00094; A61B 1/015
(Continued)

(56) References Cited

U.S. PATENT DOCUMENTS 5,152,277 A * 10/1992 Honda ............... A61B 1/00082
600/106
5,660,175 A * 8/1997 Dayal ................ A61M 16/00
128/200.26
(Continued)

FOREIGN PATENT DOCUMENTS

EP 2016914 1/2009
EP 2364637 9/2011
(Continued)

OTHER PUBLICATIONS

"International Search Report (Form PCT/ISA/210) of PCT/KR2014/010530", dated Jan. 22, 2015, pp. 1-6.
(Continued)

*Primary Examiner* — Matthew J Kasztejna
(74) *Attorney, Agent, or Firm* — JCIPRNET

(57) ABSTRACT

Disclosed are a device and method for fixing and shortening the bowel at the time of endoscopy. The device and method can improve the shortening efficiency of the bowel when compared with the existing endoscope surgery, reduce the inspection time, and mitigate patient inconvenience. Furthermore, an endoscope machine that has been used by an operator can be used, thereby facilitating an operation, and the machine itself need not be separately purchased, thereby obtaining a cost reduction effect. Furthermore, through the application of principles of the device and method, a colonoscopy which is difficult due to the formation of a loop, or retrograde cholangiopancreatography inspection and treatment of a patient having an abnormal anatomical structure due to an operation can be further anticipated.

9 Claims, 5 Drawing Sheets

(51) Int. Cl.
*A61B 1/00* (2006.01)
*A61B 1/015* (2006.01)
*A61B 1/273* (2006.01)
*A61B 17/00* (2006.01)

(52) U.S. Cl.
CPC ...... *A61B 1/00094* (2013.01); *A61B 1/00135* (2013.01); *A61B 1/00147* (2013.01); *A61B 1/00154* (2013.01); *A61B 1/015* (2013.01); *A61B 1/2736* (2013.01); *A61B 2017/00296* (2013.01); *A61B 2017/00818* (2013.01)

(58) Field of Classification Search
USPC .................. 600/114–115, 121–125, 156
See application file for complete search history.

(56) References Cited

U.S. PATENT DOCUMENTS 5,855,569 A * 1/1999 Komi ............... A61B 10/04
604/103

2005/0137457 A1 * 6/2005 Machida ............ A61B 1/00082
600/115
2008/0228029 A1 9/2008 Mikkaichi et al.
2008/0281155 A1 * 11/2008 Fujikura ............ A61B 1/00082
600/115
2013/0281781 A1 * 10/2013 Farhadi .............. A61B 1/00147
600/116

FOREIGN PATENT DOCUMENTS

| | | |
|---|---|---|
| JP | 2005-261857 | 9/2005 |
| JP | 2007-061398 | 3/2007 |
| JP | 2007-268137 | 10/2007 |
| JP | 2009022443 | 2/2009 |
| KR | 10-0471653 | 3/2005 |
| WO | 2004071284 | 8/2004 |

OTHER PUBLICATIONS

"Office Action of Japan Counterpart Application", dated Nov. 29, 2016, p. 1-p. 5, in which the listed references were cited.

* cited by examiner

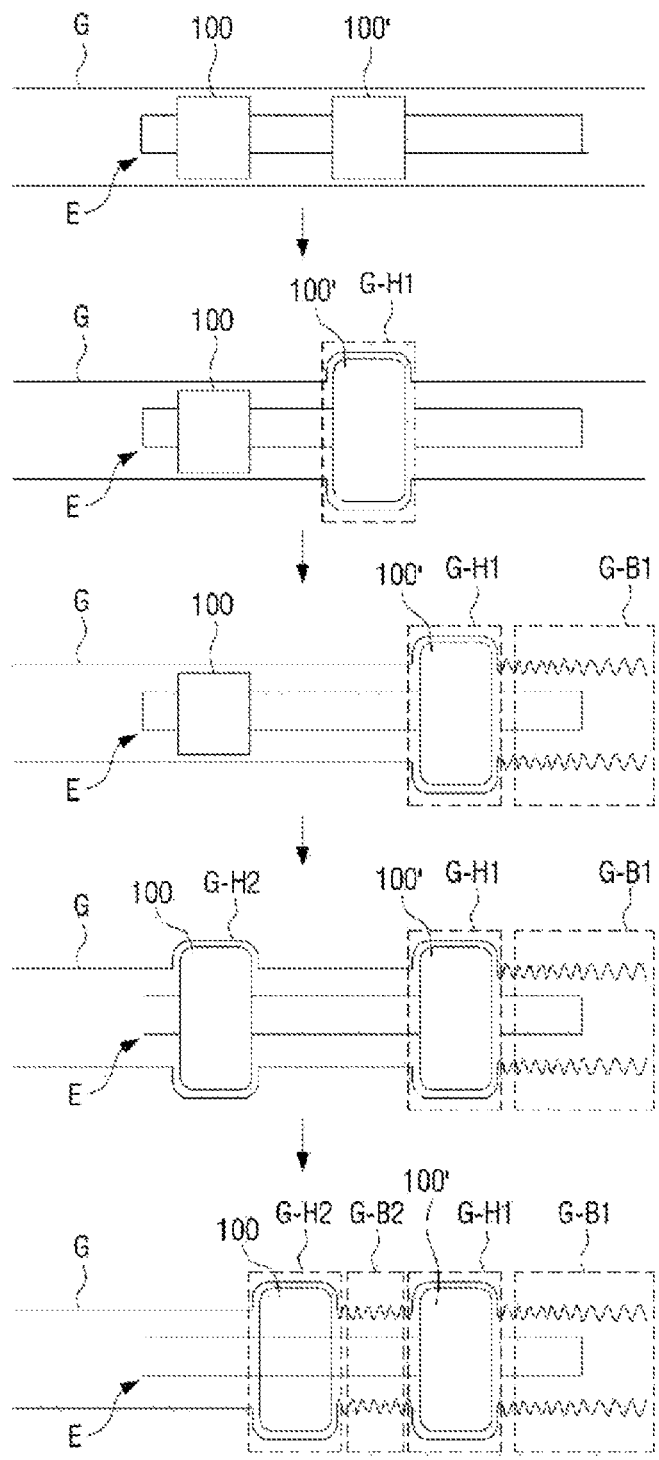

APPARATUS AND METHOD FOR FIXING AND SHORTENING BOWEL AT THE TIME OF ENDOSCOPY

CROSS-REFERENCE TO RELATED APPLICATION

This application is a 371 application of an International PCT application serial no. PCT/KR2014/010530, filed on Nov. 4, 2014, which claims the priority benefits of Korean application no. KR 10-2013-0132907, filed on Nov. 4, 2013. The entirety of each of the above-mentioned patent applications is hereby incorporated by reference herein and made a part of this specification.

TECHNICAL FIELD

The present invention relates to an apparatus and method for fixing and shortening a bowel at the time of endoscopy, which is installed at an existing endoscope to fix and shorten an inner wall of the bowel and thus to allow the existing endoscope to easily move in the bowel, thereby enabling observation and a medical treatment procedure of a site where the observation is difficult or impossible through only an existing endoscopic instrument.

BACKGROUND ART

An endoscope is a medical instrument which allows direct observation of internal organs and insides of body cavities in a human body, and may also refer to an entire process including observation of a patient and a medical treatment procedure using the endoscope. Hereinafter, 'endoscopy' or 'endoscopic procedure' is defined as a term which refers to the observation or the medical treatment procedure of internal organs of a patient using the endoscope, and the 'endoscopic instrument' or 'endoscope apparatus' is defined as an endoscope which is a medical instrument which is used in the endoscopic procedure.

In the observation of the internal organs and the insides of the body cavities in the human body through the endoscopic procedure, a site where the observation is the most difficult is the intestine tenue which may be referred to as the small bowel. This is because, unlike the stomach or the large bowel where the endoscopic procedure is mainly performed, the small bowel is not fixed to a certain part of the human body, has a long length and performs peristalsis. Therefore, it is not easy to perform the endoscopy in the small bowel, compared with other organs, and the existing endoscope has a limitation in solving such a difficulty.

Due to such a problem, a capsule endoscope is generally used for observation and diagnosis of an inside of the small bowel.

The capsule endoscope is a vitamin pill-sized endoscope which includes a lens, a light emitting element, an image recording unit, a battery, a wireless transmission unit, an antenna and so on, and a user inserts the capsule endoscope through the mouth. The capsule endoscope photographs the small bowel while moving from the mouth to the rectum, and stores the photographed images in an external recording unit through wireless communication.

However, since it is not possible to remotely control the capsule endoscope, and a photographing direction and angle are determined according to movements of the capsule endoscope, there is a limitation in the observation of the small bowel and also it is not possible to repeatedly perform a checkup. Also, since a size thereof should be minimized, it is difficult to install an additional unit, and thus it is not possible to perform a biopsy or the like.

To overcome the problems in the capsule endoscope and to perform the biopsy or a medical treatment of a corresponding area when a small bowel disease is suspected or confirmed, a double balloon endoscope has been developed. The double balloon endoscope which has been used with FDA and Korean Food and Drugs Administration (KFDA) approval since 2004 performs the endoscopy while being moved along the narrow and winding small bowel and a balloon installed at each end of an over-tube, the endoscope and the over-tube are operated. In general, since it is difficult to move along the entire small bowel having a length of about 6 m at one time, it is determined which of a mouth side and an anus side is closer to a lesion, and then the endoscopy is usually performed in one direction or twice in both directions.

Among the endoscopes developed so far, the double balloon endoscope may be most deeply inserted into the human body, and thus may effectively perform the treatment or the biopsy for the small bowel disease. However, the double balloon endoscope has some disadvantages in that a new high-priced endoscope should be purchased to perform the endoscopic procedure, a long procedural time is taken, compared with existing endoscopy, and also a high skill level of the user is required due to a high degree of difficulty in the procedure. Also, since the patient has great pain and discomfort, and the procedure using the endoscope imposes a heavy financial burden on the patient, the endoscope is not used universally.

The small bowel may be divided into a duodenum, a jejunum and an ileum from the stomach. The duodenum is firmly fixed to a posterior abdominal wall, but the jejunum and the ileum which are the majority of the small bowel are not fixed but extend long in an abdominal cavity. Due to such a structure of the small bowel, the endoscopic procedure for the small bowel may not be effectively performed even using the double balloon endoscope. To perform the endoscopy procedure, a string-shaped endoscope scope connected to a main body of the endoscope should be basically pushed and inserted into the human body. As the endoscope scope is inserted into the small bowel, the small bowel which is not fixed is pushed and stretched, and thus the patient's discomfort and pain intensify.

As another problem in the double balloon endoscope, an accessorial over-tube should be additionally used when the new endoscope is used. After the endoscope moves along the small bowel, the over-tube is pushed and inserted. At this time, use of only the over-tube has a limitation in overcoming the problem that the small bowel is pushed and stretched. Also, since a length of the over-tube is fixed and not varied, and the endoscope is used while being inserted therein, it is inconvenient for use, compared with the existing endoscope.

As described above, the double balloon endoscope may not effectively shorten the small bowel, and thus the procedural time is increased, and the patient's pain intensifies.

Therefore, an endoscope for observing the small bowel, rather than the existing procedure devices or an effective method for, observing the small bowel is required.

As the above-described endoscope for observing the small bowel, an endoscope which is invented to observe a narrow space, such as the small bowel, in the human body is disclosed in Korean Patent No. 10-0471653. The registered patent relates to an endoscope system including a head part which has a camera unit installed at one side of a hollow cylindrical part, the hollow cylindrical part which is connected with a tube connected to an external device located outside a human body at the other side thereof, a front fixing part which is connected with the head part and installed at an outer circumference of the cylindrical part to be fixed to an internal wall of an organ, a rear fixing part which is installed at the outer circumference of the cylindrical part to be slidable on an outer circumferential surface of the cylindrical part and also to be fixed to the internal wall of the organ, and a moving part which elongates or contracts between the front fixing part and the rear fixing part so as to move the head part in the organ when the front fixing part or the rear fixing part fixes the head part to the internal wall of the organ.

The registered patent may theoretically observe the small bowel, but relates to a mechanical endoscope which is complicatedly operated, unlike the existing endoscope. Accordingly, even though a user is experienced in the existing endoscopic procedure, it is difficult for the user to use it, and also to actually operate it due to a risk of malfunction, and it is necessary to separately purchase a new specific endoscope, and thus it is uneconomical.

Also, the registered patent is different from the existing endoscope in the basic principle and an operation method, is incompatible therewith. In addition, it is difficult to perform various procedures such as a biopsy, removing of polyps and a styptic treatment performed in the existing endoscope procedures, and an additional apparatus is required, and thus actual utility in a clinic is limited.

SUMMARY

Technical Problem

The present invention is directed to providing an apparatus and method for fixing and shortening a bowel at the time of endoscopy, which is installed at an existing endoscope to fix a main device in the bowel and also to shorten the bowel according to a user's operation.

Technical Solution

One aspect of the present invention provides a bowel fixing apparatus for fixing and shortening a bowel at the time of an endoscopy, including an external frame of which an inside is formed in a hollow cylindrical shape so that an endoscope passes therethrough; a loop-shaped external cuff which is installed to surround an outer surface of the external frame; an internal cuff which is installed to be attached to an inner surface of the external frame; a lubricant tube which is located at the inner surface of the external frame; and a suction tube, wherein an external cuff tube is installed at one side of the external cuff and an internal cuff tube is installed at one side of the internal cuff so that each of the external cuff and the internal cuff is able to contract or expand according to discharge or introduction of a gas.

The internal cuff may be located between the loop-shaped external frame and the endoscope, and the endoscope and the external frame may be fixed while the internal cuff expands.

The lubricant tube and the suction tube may be installed to be attached to a side surface of the internal cuff.

An external operator may inject or discharge the gas through the external cuff tube connected to the external cuff and may also inject or discharge the gas through the internal cuff tube connected to the internal cuff, and the operator may inject a physiological saline solution into the external cuff, the internal cuff and the endoscope through the lubricant tube, and may also remove air or liquid in the bowel through the suction tube.

While the external cuff expands, a fixing position may be formed at the bowel, and the endoscope and the bowel fixing apparatus may be separated from each other, as the gas in the internal cuff is discharged.

At least one bowel fixing apparatus may be installed at one endoscope.

Another aspect of the present invention provides a method for observing or performing a procedure on the deep site in the human body which is difficult to observe without a device, in which an endoscope is inserted into a patient's body and the endoscopy is performed, wherein at least one apparatus is installed at an outside of the endoscope, and the apparatus is fixed to a certain portion of a body organ, in which the endoscope is inserted, using the apparatus, and an operator separates the endoscope from the apparatus, pulls the apparatus and thus shortens a length of the body organ fixed to the apparatus.

A bowel fixing apparatus may be used as an apparatus which is installed at an outside of the endoscope.

Advantageous Effects

According to the present invention, the endoscope at which the apparatus of the present invention is installed is located in the small bowel, and the small bowel and the apparatus are fixed to each other using the apparatus, and the rear portion of the fixed small bowel is pulled so that the small bowel is folded and thus a length of the bowel is shortened, and then the endoscopy is performed. The shortening efficiency of the bowel is higher than the existing endoscopy, and the inspection time may be reduced, and the patient discomfort may also be reduced. Further, since the endoscopic instrument that has been used by an operator may be used, the operator may easily perform the procedure, and also since it is not necessary to separately purchase the machine, it is possible to obtain a cost reduction effect.

Furthermore, through the application of principles of the apparatus and method, a colonoscopy which is difficult due to the formation of a loop, or retrograde cholangiopancreatography inspection and treatment of a patient having an abnormal anatomical structure due to a procedure may be further anticipated.

BRIEF DESCRIPTION OF THE DRAWINGS

FIGS. 4A-4E are structural views illustrating a process of inserting the endoscope into the small bowel using two bowel fixing apparatuses according to another embodiment of the present invention.

DESCRIPTION OF THE EMBODIMENTS

Hereinafter, exemplary embodiments of the present invention will be described in detail with reference to the accompanying drawings. However, the present invention is not limited to the exemplary embodiments disclosed below, but can be implemented in various forms. It would be appreciated by those skilled in the art that changes may be made in these embodiments without departing from the principles and spirit of the invention, the scope of which is defined in the claims and their equivalents.

Figure 1:
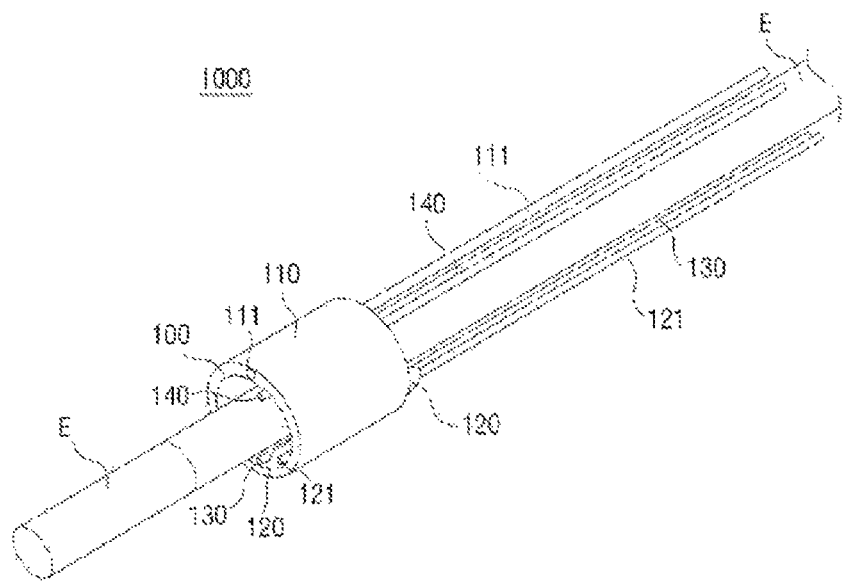
FIG. 1 is a perspective view of a bowel fixing apparatus according to one embodiment of the present invention.

FIG. 1 is a perspective view of a bowel fixing apparatus according to one embodiment of the present invention, and FIGS. 2A-2D are cross-sectional views of the bowel fixing apparatus according to one embodiment of the present invention.

Referring to FIGS. 1 and 2A-2D, a configuration and an installation structure of a bowel fixing apparatus 1000 of the present invention will be described. The bowel fixing apparatus 1000 includes a short hollow cylindrical external frame 100 which enables an endoscope E to pass therethrough, an external cuff 110 which is attached and installed to surround an outside of the external frame, an external cuff tube 111 which is installed at one side of the external cuff 110, an internal cuff 120 which is attached to an inside of the external frame 100 to be interposed between the external frame 100 and the endoscope E, an internal cuff tube 121 which is installed at one side of the internal cuff 120, and a lubricant tube 130 and a suction tube 140 which are installed inside the external frame 100.

Here, the external cuff 110 is formed in a loop tube shape which surrounds the external frame 100, as illustrated in FIGS. 1 and 2A-2D, and the internal cuff 120 is attached to the inside of the external frame 100 to be interposed between the external frame 100 and the endoscope E, as illustrated in FIG. 1, and may have a cylindrical shape or an oval tube shape, but is not limited thereto.

Also, the external cuff 110 and the internal cuff 120 may be formed of a material, such as vinyl, rubber and plastic, that allows expansion or contraction when a gas to be injected therein, but are not limited thereto.

As illustrated in FIGS. 1 and 2A-2D, the lubricant tube 130 and the suction tube 140 are attached to the inside of the external frame 100 or attached to a side surface of the internal cuff 120.

Here, the tubes 111, 121, 130 and 140 are formed in a thin and flexible tubular shape which is bent while maintaining an inner diameter thereof, and may be formed of a plastic material having durability, but are not limited thereto.

As illustrated in FIG. 1, the above-described bowel fixing apparatus 1000 is installed to surround a side surface of the endoscope E. Therefore, the bowel fixing apparatus 1000 has the following functions. First, the external cuff 110 serves to contract or expand so as to enable the bowel fixing apparatus 1000 inserted into the small bowel to be fixed at a certain position of the small bowel, and the internal cuff 120 serves to contract or expand between the external frame 100 and the endoscope E so as to attach or detach the external frame 100 and the external cuff 110 to/from the endoscope E.

To perform the contraction or the expansion of the external cuff 110, one end of the external cuff tube 111 installed at a side surface of the external cuff 110 is installed at the external cuff 110 so as to enable the gas to be injected therein, and the other end thereof is opened and exposed so as to enable an external operator to inject the gas into the external cuff 110 through the external cuff tube 111. Due to such a configuration, the operator is able to inject or discharge the gas into/from the external cuff 110 through the other end of the external cuff tube 111 so that the external cuff 110 may expand or contract.

In the same manner, to perform the contraction or the expansion of the internal cuff 120, one end of the internal cuff tube 121 installed at the side surface of the internal cuff 120 is installed at the internal cuff 120 so as to enable air to be injected therein, and the other end thereof is opened and exposed so as to enable the external operator to inject the gas into the internal cuff 120 through the internal cuff tube 121. Due to such a configuration, the operator is able to inject or discharge the gas into/from the internal cuff 120 through the other end of the internal cuff tube 121 so that the internal cuff 120 may expand or contract.

The lubricant tube 130 attached to the side surface of the internal cuff 120 is installed so that one end thereof is attached to the inside of the external frame 100 or the side surface of the internal cuff 120 in an opened state and the other end thereof is opened and exposed to the external operator. Accordingly, when the endoscope E moves in the bowel fixing apparatus 1000, the operator may inject a lubricant formed of a physiological saline solution between the endoscope E and the external frame 100 and between the external cuff 110 and the internal cuff 120 through the other end of the lubricant tube 130 which is opened and exposed, and thus friction among the endoscope E, the external frame 100 and the internal cuff 120 may be minimized.

In the same manner, the suction tube 140 attached to the inside of the external frame 100 or the side surface of the internal cuff 120 is installed so that one end thereof is attached to the side surface of the internal cuff 120 in an opened state and the other end thereof is opened and exposed to the external operator. Accordingly, when the air is excessively injected or liquid is in the bowel while the endoscope E is inserted into the small bowel and performs the endoscopy, the external operator may suction and remove the gas and the liquid in the bowel of a patient through the other end of the suction tube 140 which is opened and exposed.

Figures 2A, 2B, 2C, 2D:
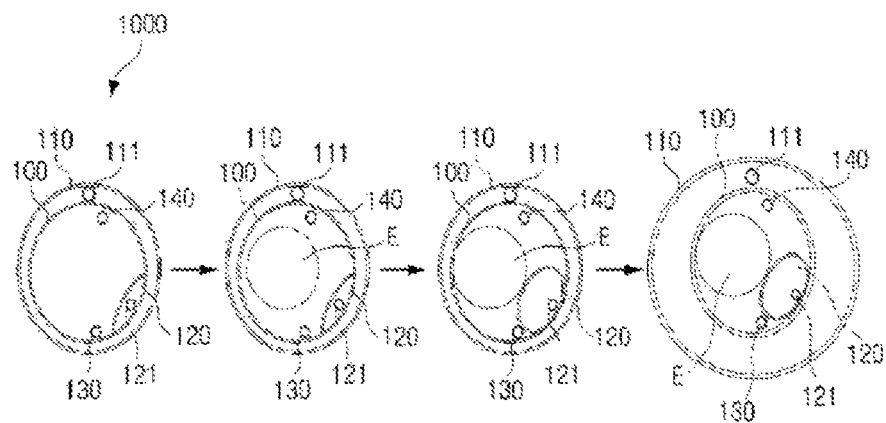
FIGS. 2A-2D are cross-sectional views of the bowel fixing apparatus according to one embodiment of the present invention.

The configuration and operation will be described in detail with reference to FIGS. 2A-2D. The bowel fixing apparatus 1000 of the present invention having the configuration as illustrated in FIG. 2A is installed so that the endoscope E is inserted into the inside of the external frame 100, as illustrated in FIG. 2B. To install the bowel fixing apparatus 1000, the internal cuff 120 attached to the external frame 100, as illustrated in FIG. 2C, is inflated while the endoscope E is inserted into the bowel fixing apparatus 1000 as illustrated in FIG. 2B, so that the endoscope E is fixed between the external frame 100 and the internal cuff 120 due to an expansive force of the internal cuff 120, and thus the bowel fixing apparatus 1000 may be fixed to the endoscope E.

As items to be careful about at this time, if the lubricant tube 130 and the suction tube 140 are pressed among the endoscope E, the external frame 100 and the internal cuff 120, the lubricant tube 130 and the suction tube 140 may not perform their own functions. To prevent the lubricant tube 130 and the suction tube 140 from being pressed, a user may install the lubricant tube 130 and the suction tube 140 at both side surfaces of the internal cuff 120 with a predetermined interval, when the lubricant tube 130 and the suction tube 140 are installed. This is to prevent the lubricant tube 130 and the suction tube 140 from being biased to one side in a process in which the small bowel is pulled and shortened using the tubes 111, 121, 130 and 140, which will be described below, and thus to prevent the external frame 100 biasedly pulled by the tubes from being caught on the endoscope E, and also to minimize a case in which the lubricant like the physiological saline solution injected through the lubricant tube 130 is suctioned again through the suction tube 140.

The endoscope E may be inserted into the small bowel while the internal cuff 120 expands and the external frame 100 is fixed to the endoscope E as illustrated in FIG. 2C, and may freely move in the small bowel, because the external cuff 110 is still in a contracted state. In a state in which the endoscope E and the bowel fixing apparatus 1000 are located in the small bowel as described above, the external cuff 110 may expand, and thus the bowel fixing apparatus 1000 may be fixed at a certain position of the small bowel, as illustrated in FIG. 2D.

Figure 5:
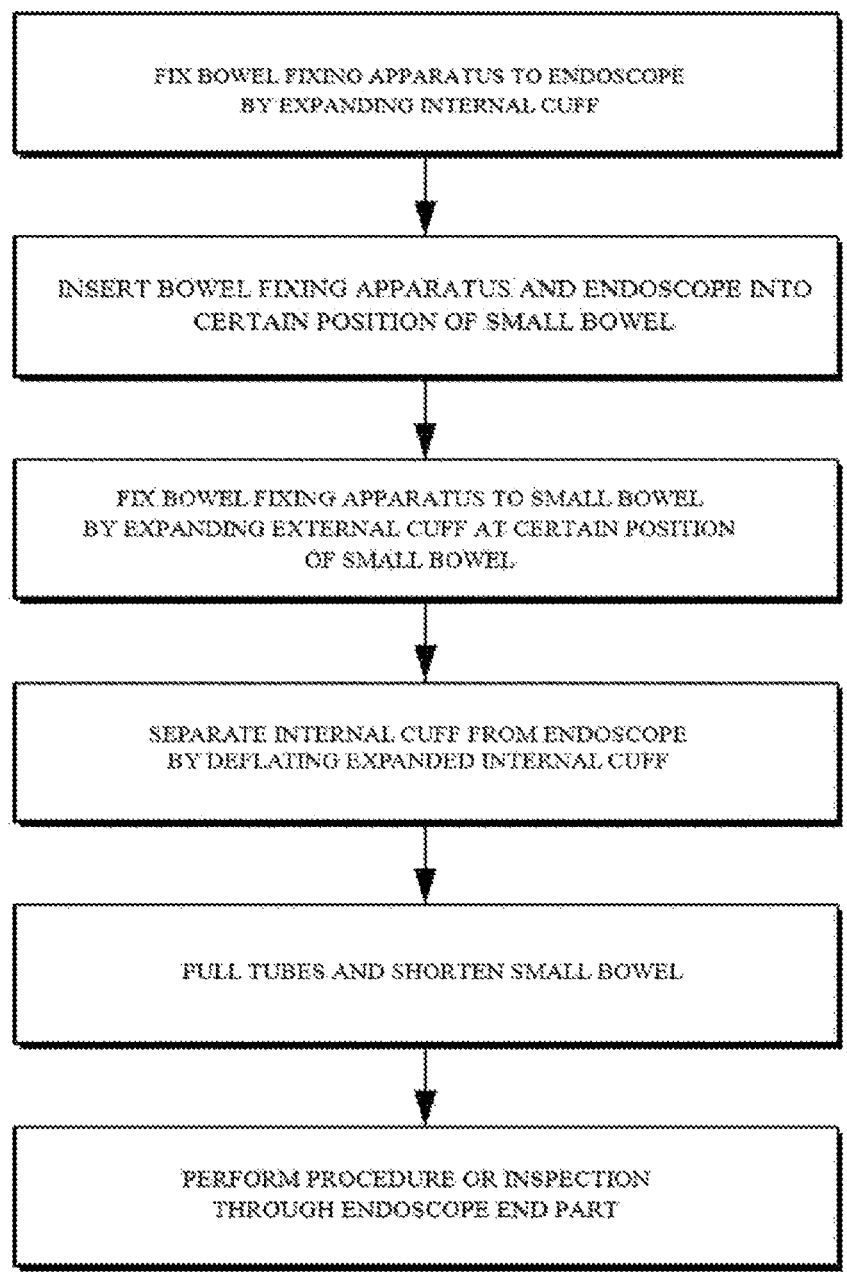
FIG. 5 is a flowchart illustrating an operation of the bowel fixing apparatus according to one embodiment of the present invention.

FIGS. 3A-3E are structural views illustrating a process of inserting the endoscope E into the small bowel G using the bowel fixing apparatus 1000 according to one embodiment of the present invention, and FIG. 5 is a flowchart illustrating an operation of the bowel fixing apparatus 1000 according to one embodiment of the present invention. Hereinafter, a process in which the bowel fixing apparatus 1000 of the present invention and the endoscope E are operated in the small bowel G will be described with reference to FIGS. 3A-3E and 5.

Figure 3A:
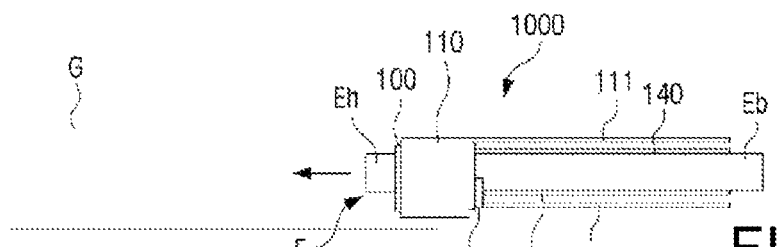
FIGS. 3A-3E are structural views illustrating a process of inserting an endoscope into a small bowel using the bowel fixing apparatus according to one embodiment of the present invention.

FIG. 3A is a structural view illustrating a state in which the bowel fixing apparatus 1000 of the present invention is being inserted into the patient's small bowel G while being fixed to an endoscope end part Eh of the endoscope E. An example in which the bowel fixing apparatus 1000 is fixed to the endoscope end part Eh of the endoscope E will be described below. However, the bowel fixing apparatus 1000 may be used while being fixed to an endoscope body Eb according to operator convenience.

Before the endoscopy is performed as illustrated in FIG. 3A, the bowel fixing apparatus 1000 is inserted in a fixed state to the endoscope end part Eh of the endoscope E. At this time, in order for the bowel fixing apparatus 1000 to be easily inserted into the small bowel G in the fixed state to the endoscope end part Eh of the endoscope E, the external cuff 110 of the bowel fixing apparatus 1000 is inserted in a contracted state, and the internal cuff 120 thereof is inserted in an expanded state, and thus the external cuff 110 may be inserted in the fixed state to the endoscope end part Eh of the endoscope E.

Figure 3B:
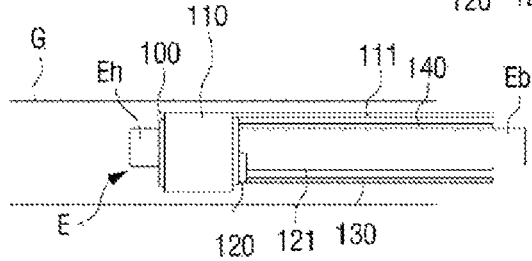

FIG. 3B illustrates a state in which the bowel fixing apparatus 1000 is inserted into the small bowel G while being fixed to the endoscope E as described above. As illustrated in FIG. 3B, in order for the endoscope E to reach a deep inside of the patient's small bowel G while being inserted into the small bowel G, the bowel fixing apparatus 1000 is fixed at a certain position of the small bowel G using the bowel fixing apparatus 1000. To this end, as illustrated in FIG. 3C, the gas is injected into the external cuff 110 to expand the external cuff 110, and thus the expanded external cuff 110 is in close contact with and fixed to a fixing position G-H of the small bowel G, and all of the endoscope E, the bowel fixing apparatus 1000 and the small bowel G are fixed at the fixing position G-H of the small bowel G.

At this time, to inject the gas into the external cuff 110, the operator may inject the gas from an outside into the external cuff 110 using the external cuff tube 111 connected to the side surface of the external cuff 110 so as to be opened.

Figure 3C:
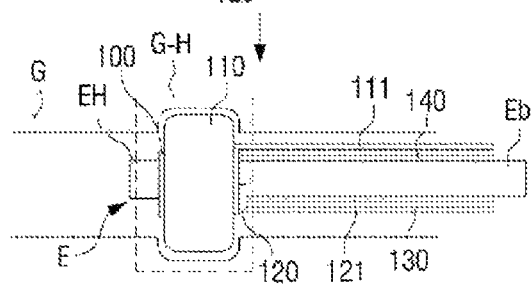
Figure 3D:
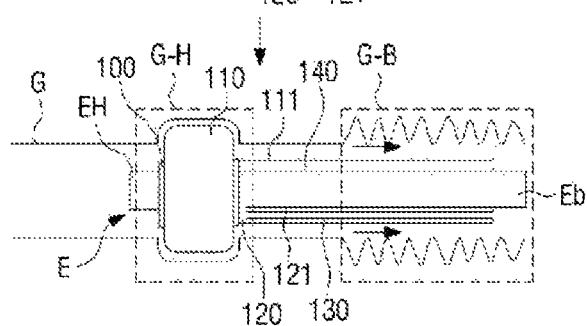

As described above, to shorten a rear portion of the small bowel G in a state in which the endoscope E and the bowel fixing apparatus 1000 are fixed to the fixing position G-H of the patient's small bowel G, as illustrated in FIG. 3C, the endoscope E and the bowel fixing apparatus 1000 are separated. This will be described with reference to FIGS. 3D and 3E. First, the user deflates and reduces the expanded internal cuff tube 121 of the bowel fixing apparatus 1000, and thus separates the bowel fixing apparatus 1000 from the endoscope E.

Then, the physiological saline solution is injected through the lubricant tube 130 of the bowel fixing apparatus 1000. This is to reduce the friction between the bowel fixing apparatus 1000 and the endoscope E and also to prevent damage to the bowel fixing apparatus 1000 and the endoscope E.

Figure 3E:
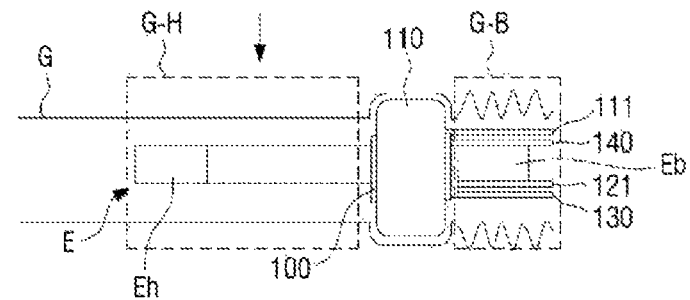

If the four tubes 111, 121, 130 and 140 of the bowel fixing apparatus 1000 are slowly pulled while the physiological saline solution is injected between the bowel fixing apparatus 1000 and the endoscope E through the lubricant tube 130, the fixing position G-H of the small bowel G is also pulled, and a shortened portion G-B is formed while a rear portion of the fixing position G-H is crumpled. In this case, the endoscope E is separated from the bowel fixing apparatus 1000 and thus actually stopped. However, since the front portion of the small bowel G is dragged through a process in which the shortened portion G-B of the bowel fixing apparatus 1000 is formed, and the endoscope end part Eh of the endoscope E may move forward to the front portion of the small bowel G as illustrated in FIG. 3E.

At this time, while the endoscope E and the bowel fixing apparatus 1000 separately move, the internal and external cuff tubes 111 and 121, the lubricant tube 130 and the suction tube 140 which are connected with the bowel fixing apparatus 1000 are pulled with the same force, and thus the rear portion G-B of the small bowel G may be maintained in a shortened state.

Also, the tubes 111, 121, 130 and 140 should be arranged in consideration of a pulling force applied to the bowel fixing apparatus 1000. If the tubes 111, 121, 130 and 140 are arranged at the bowel fixing apparatus 1000 to be biased to one side, a direction of a force applied to the external frame 100 of the bowel fixing apparatus 1000 leans to a direction in which the tubes are located in the process in which the shortened portion G-B is formed, and thus the endoscope E and the bowel fixing apparatus 1000 may be caught on each other. Therefore, the user should arrange the tubes 111, 121, 130 and 140 to be uniformly distributed in consideration of positions of the tubes.

The suction tube 140 installed at the side surface of the internal cuff 120 serves to suction the air or the liquid in the bowel G expanded by injection of the air or the like occurring when the endoscopy is performed so as to assist in effectively shortening and fixing the bowel. As illustrated in FIG. 1, one end of the suction tube 140 is attached and fixed to the inside of the bowel fixing apparatus 1000 to be opened, and the other end thereof is exposed to the outside so that the operator may apply a negative pressure through the other end of the suction tube 140, may suction the gas and the liquid in the bowel, thereby restricting expansion of the small bowel, and also may smoothly perform the endoscopy and the treatment of the small bowel.

When the endoscope E is withdrawn to the outside, the external cuff 110 contracts, and the internal cuff 120 expands, and thus the bowel G is separated from the bowel fixing apparatus 1000 while the endoscope E and the bowel fixing apparatus 1000 are fixed, and thus the endoscope E and each tube may smoothly move back and may be withdrawn.

Figure 6:
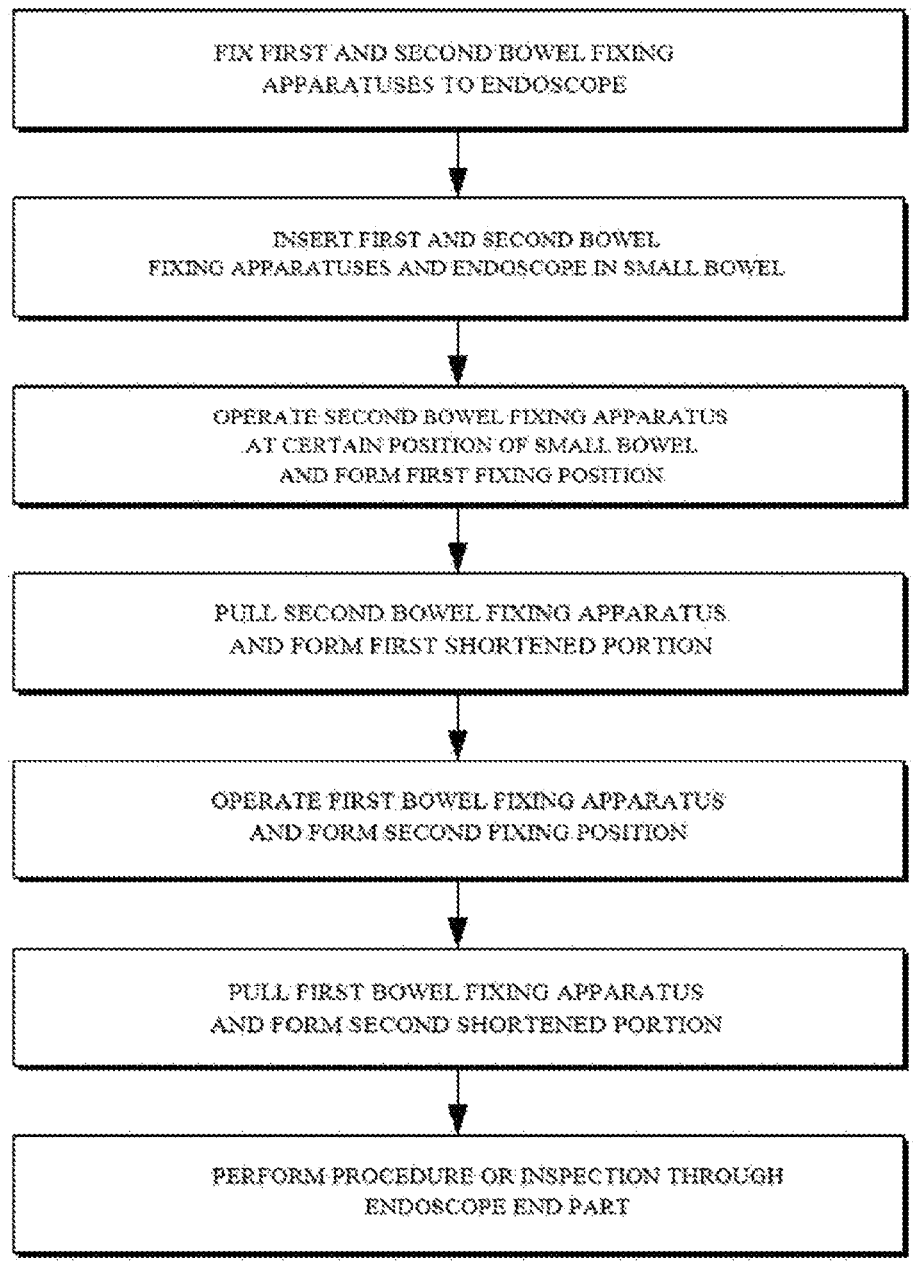
FIG. 6 is a flowchart illustrating an operation of the bowel fixing apparatuses according to another embodiment of the present invention.

Until now, the bowel fixing apparatus 1000 according to one embodiment of the present invention has been described with reference to FIGS. 1 to 3A-3E and 5. However, this is only one embodiment for understanding of the present invention and convenience of description, and the present invention is not limited thereto. For example, FIGS. 4A-4E are structural views illustrating a process in which the endoscope E is inserted into the small bowel G to observe or treat the bowel using two bowel fixing apparatuses 1000 and 1000' according to another embodiment of the present invention, and FIG. 6 is a flowchart for operating the endoscope E in the bowel G using the two or more bowel fixing apparatuses 1000 and 1000'. Also, the endoscope E may be inserted into the small bowel G to observe or treat the bowel using three or more bowel fixing apparatuses of the present invention.

Hereinafter, another embodiment of the present invention in which the endoscope E is inserted into the small bowel G using the two bowel fixing apparatuses 1000 and 1000' will be described with reference to FIGS. 4A-4E and 6.

The two bowel fixing apparatuses 1000 and 1000' are installed at a side surface of the endoscope E to be spaced apart from each other at a certain distance. A method for fixing the two bowel fixing apparatuses 1000 and 1000' to the endoscope E and a method for operating the two bowel fixing apparatuses 1000 and 1000' in the bowel are the same as the methods illustrated in FIGS. 2A-2D, and a configuration of each of the two bowel fixing apparatuses 1000 and 1000' is the same as that illustrated in FIG. 1. In another embodiment of the present invention, an example in which the suction tube 140 is installed at the first bowel fixing apparatus 1000 to be operated will be described.

As illustrated in FIG. 4A, the endoscope E to which the first and second bowel fixing apparatuses 1000 and 1000' are fixed is inserted into the small bowel G.

In a state in which the endoscope E is inserted into the small bowel G as illustrated in FIG. 4A, the operator operates the second bowel fixing apparatus 1000' to form a first fixing position G-H1 at a certain position of the small bowel G, and fixes the endoscope E and the second bowel fixing apparatus 1000' to the small bowel G.

In a state in which the first fixing position G-H1 is formed by operating the second bowel fixing apparatus 1000' in the small bowel G, the operator separates the second bowel fixing apparatus 1000' from the endoscope, and then, shortens the bowel located at a rear side of the first fixing position G-H1 of the small bowel G while softly pulling the small bowel G to which the second bowel fixing apparatus 1000' is fixed using the tube installed at the second bowel fixing apparatus 1000', thereby forming a first shortened portion G-B1. As the small bowel G is shortened due to formation of the first shortened portion G-B1, the endoscope end part Eh of the endoscope E relatively moves forward in the inside of the small bowel G.

In a state in which the first shortened portion G-B1 is formed in the small bowel G and thus the endoscope E and the first bowel fixing apparatus 1000 move forward in the inside of the small bowel G, as illustrated in FIG. 4C, the operator operates the first bowel fixing apparatus 1000 according to the process described through FIGS. 2A-2D, and forms a second fixing position G-H2 in the small bowel G, as illustrated in FIG. 4D.

In a state in which the operator operates the first bowel fixing apparatus 1000 and forms the second fixing position G-H2 in the small bowel G, the operator softly pulls the tubes installed at the first bowel fixing apparatus 1000 to reduce a distance between the first fixing position G-H1 and the second fixing position G-H2 of the small bowel G, as illustrated in FIG. 4E, thereby forming a second shortened portion G-B2. Accordingly, the endoscope end part Eh of the endoscope E relatively moves forward in the inside of the small bowel by a length shortened through the second shortened portion G-B2 of the small bowel G, and thus operator may perform and complete a desirable procedure through the endoscope end part Eh of the endoscope E.

The operation and process of the bowel fixing apparatuses 1000 and 1000' in the endoscope E in FIGS. 4A-4E and 6 are another embodiment of the present invention using the two bowel fixing apparatuses 1000 and 1000'. When three or more bowel fixing apparatuses are used in the endoscope E, the small bowel may be shortened in the same method, and thus the endoscope may move forward in the small bowel.

What is claimed is:

1. A bowel fixing apparatus for fixing and shortening a bowel at the time of an endoscopy, comprising:
   an external frame of which an inside is formed in a hollow cylindrical shape so that an endoscope passes therethrough;
   a loop-shaped external cuff which is installed to surround an outer surface of the external frame;
   an internal cuff which is installed to be attached to a part of an inner surface of the external frame;
   a lubricant tube which is located at the inner surface of the external frame and the lubricant tube is extended along a length of the inner surface; and
   a suction tube,
   wherein an external cuff tube is installed at one side of the external cuff and an internal cuff tube is installed at one side of the internal cuff so that each of the external cuff and the internal cuff is able to contract or expand according to discharge or injection of a gas,
   wherein the internal cuff is attached to the inside of the external frame to be interposed between the external frame and the endoscope, and
   an opening is defined by surfaces of the external frame, the endoscope and the internal cuff,
   wherein the internal cuff is inflated to securely position the endoscope within the external frame, so that the opening is defined between the surfaces of the external frame, the endoscope and the internal cuff which is inflated; and
   the lubricant tube and the suction tube are disposed in the opening, so that suction and/or lubrication is provided through the opening defined by the surfaces of the external frame, the endoscope and the inflated internal cuff.

2. The bowel fixing apparatus of claim 1, wherein the internal cuff is located between the loop-shaped external frame and the endoscope, and the endoscope and the external frame are able to be fixed while the internal cuff expands.

3. The bowel fixing apparatus of claim 1, wherein an external operator is able to inject or discharge the gas through the external cuff tube connected to the external cuff and also able to inject or discharge the gas through the internal cuff tube connected to the internal cuff.

4. The bowel fixing apparatus of claim 1, wherein a physiological saline solution is able to be injected between the endoscope and the external frame through the lubricant tube.

5. The bowel fixing apparatus of claim 1, wherein air or liquid in the bowel is able to be removed through the suction tube.

6. The bowel fixing apparatus of claim 1, wherein the bowel is shortened by pulling the fixed bowel fixing apparatus using the internal and external cuff tubes, the lubricant tube and the suction tube which are exposed to an outside of a human body while using the bowel fixing apparatus.

7. The bowel fixing apparatus of claim 1, wherein at least one bowel fixing apparatus is capable of being applied to one endoscope.

8. The bowel fixing apparatus of claim 1, wherein a fixing position is formed at the bowel, while the external cuff expands.

9. The bowel fixing apparatus of claim 1, wherein the endoscope and the bowel fixing apparatus are separated from each other, as the gas in the internal cuff is discharged.

* * * * *